(12) United States Patent
Ismail

(10) Patent No.: US 11,576,800 B2
(45) Date of Patent: Feb. 14, 2023

(54) LOW RISK, REVERSIBLE, WEIGHT LOSS PROCEDURE

(71) Applicant: Nassar Ismail, Dover, MA (US)

(72) Inventor: Nassar Ismail, Dover, MA (US)

(*) Notice: Subject to any disclaimer, the term of this patent is extended or adjusted under 35 U.S.C. 154(b) by 368 days.

(21) Appl. No.: 16/441,965

(22) Filed: Jun. 14, 2019

(65) Prior Publication Data
US 2020/0390581 A1   Dec. 17, 2020

(51) Int. Cl.
*A61F 5/00* (2006.01)
*A61B 5/00* (2006.01)

(52) U.S. Cl.
CPC .......... *A61F 5/0086* (2013.01); *A61F 5/0063* (2013.01); *A61B 5/4238* (2013.01); *A61F 5/0036* (2013.01)

(58) Field of Classification Search
CPC ........ A61F 5/0036–0046; A61F 5/0083–0086; A61F 5/0013–0089; A61F 5/1204; A61F 5/005–0063; A61B 2017/00287
See application file for complete search history.

(56) References Cited

U.S. PATENT DOCUMENTS

| | | | |
|---|---|---|---|
| 5,947,983 A * | 9/1999 | Solar | A61B 17/0469 604/22 |
| 7,189,247 B1 | 3/2007 | Zirps et al. | |
| 8,585,715 B2 | 11/2013 | Hoffman et al. | |
| 2002/0183768 A1* | 12/2002 | Deem | A61B 17/064 606/151 |
| 2004/0092892 A1* | 5/2004 | Kagan | A61F 2/04 604/264 |
| 2004/0153106 A1* | 8/2004 | Dudai | A61F 5/0066 606/157 |
| 2005/0251166 A1* | 11/2005 | Vaughan | A61B 17/0401 606/153 |
| 2005/0261712 A1* | 11/2005 | Balbierz | A61B 17/12009 606/153 |
| 2008/0249539 A1* | 10/2008 | Stokes | A61F 5/0086 606/142 |
| 2008/0319435 A1* | 12/2008 | Rioux | A61F 5/005 606/33 |
| 2009/0255544 A1* | 10/2009 | Cox | A61B 17/0401 128/898 |
| 2009/0275967 A1* | 11/2009 | Stokes | A61F 5/0083 606/172 |
| 2010/0145324 A1* | 6/2010 | Nihalani | A61F 5/0013 606/14 |

(Continued)

OTHER PUBLICATIONS

Grimm IS, Kroch DA, and Brill JV. Reimbursement for endoscopic innovations: the final hurdle. Gastrointestinal endoscopy. 2019;89: 274-276.

(Continued)

*Primary Examiner* — Catherine B Kuhlman
(74) *Attorney, Agent, or Firm* — Lambert Shortell & Connaughton; David J. Connaughton, Jr.; Justin P. Tinger

(57) ABSTRACT

A surgical weight loss procedure to reduce stomach volume is provided. The procedure involves gathering together a quantity of stomach tissue and securing this tissue together in a gathered position, which can reduce the volume of the stomach. This reduced stomach volume allows a patient to feel satiated with a much smaller amount of food, leading to weight loss.

19 Claims, 4 Drawing Sheets

(56) References Cited

U.S. PATENT DOCUMENTS

2010/0312047 A1* 12/2010 Forsell ............... A61B 17/30
                                                                                           600/37
2012/0095484 A1* 4/2012 Dominguez .......... A61F 5/0086
                                                                                           606/157

OTHER PUBLICATIONS

Jirapinyo P, Thompson CC. Focused Review seRies: Updates on endoscopic bariatric and metabolic therapies Training in Bariatric and Metabolic Endoscopic Therapies. Clin Endosc. 2018;51:430-438. doi:10.5946/ce.2018.148.

Kim DD, Basu A. Estimating the medical care costs of obesity in the United States: systematic review, meta-analysis, and empirical analysis. Value Health 2016;19: 602-13. https://doi.org/10.1016/j.jval.2016.02.008 [PMID:27565277].

Hales CM, Fryar CD, Carroll MD, Freedman DS, Ogden CL. Trends in obesity and se-vere obesity prevalence in US youth and adults by sex and age, 2007-2008 to 2015-2016. JAMA 2018;319:1723-5. https://doi.org/10.1001/jama.2018.3060 [PMID:29570750].

Colquitt JL, Pickett K, Loveman E, Frampton GK. Surgery for weight loss in adults. Cochrane Database Syst Rev 2014:CD003641. https://doi.org/10.1002/14651858.CD003641.pub4 [PMID:25105982].

Collaborators GBD, Afshin A, Forouzanfar MH, et al. Health effects of overweight and obesity in 195 countries over 25 years. N Engl J Med 2017;377(1):13-27.

Finkelstein EA, Trogdon JG, Cohen JW, Dietz W. 2009. Annual medical spending attributable to obesity: payer-and service-specific estimates. Health Aff (Millwood) 28:w822-w831 [PubMed: 19635784].

Acosta A, Abu Dayyeh BK, Port JD, Camilleri M. Recent advances in clinical practice challenges and opportunities in the management of obesity. Gut 2014;63(4):687-95.

Grill HJ, Hayes MR. Hindbrain neurons as an essential hub in the neuroanatomically distributed control of energy balance. Cell Metab 2012;16(3):296-309.

Szarka LA, Camilleri M. Gastric emptying. Clin Gastroenterol Hepatol 2009;7(8):823-7. 32.

Nunez W, Ozaki M, Vinagre A, Collares E, de Almeida E. Neural mechanisms and delayed gastric emptying of liquid induced through acute myo-cardial infarction in rats. Arq Bras Cardiol 2015;104(2):144-51.

Camilleri M. Clinical practice. Diabetic gastroparesis. N Engl J Med (2007) 356(8):820-9. doi:10.1056/NEJMcp062614.

Camilleri M, Breen M, Ryks M, Burton D. Proximal and overall gastric emp-tying of solids in patients with reduced gastric volume accommodation com-pared to matched controls. Dig Dis Sci (2011) 56(6):1729-34. doi:10.1007/s10620-011-1615-0].

Parthasarathy G, Kudva YC, Low PA, Camilleri M, Basu A, Bharucha AE. Relationship between gastric emptying and diurnal glycemic control in type 1 diabetes mellitus: a randomized trial. J Clin Endocrinol Metab (2017) 102(2):398-406. doi:10.1210/jc.2016-2809].

De Jong JR, van Ramshorst B, Gooszen HG, Smout AJ, Tiel-Van Buul MM. 2009. Weight loss after laparoscopic adjustable gastric banding is not caused by altered gastric emptying. Obes Surg 19:287-292 [PubMed: 18937018].

Yehoshua RT, Eidelman LA, Stein M, Fichman S, Mazor A, Chen J, Bemstine H, Singer P, Dickman R, Beglaibter N, Shikora SA, Rosenthal RJ, Rubin M. 2008. Laparoscopic sleeve gastrectomy: volume and pressure assessment. Obes Surg 18:1083-1088 [PubMed: 18535864.

Sagner M, Rogula T. 2003. Laparoscopic reoperative sleeve gastrectomy for poor weight loss after biliopancreatic diversion with duodenal switch. Obes Surg 13:649-654 [PubMed: 12935370].

Miller K, Hell E. 2003. Laparoscopic surgical concepts of morbid obesity. Langenbecks Arch Surg 388:375-384 [PubMed: 14586660].

Stefater MA, Wilson-Pérez HE, Chambers AP, Sandoval DA, Seeley RJ. All bariatric surgeries are not created equal: Insights from mechanistic comparisons. Endocr Rev. 2012;33(4):595-622. doi:10.1210/er.2011-1044.

T. H. Somervell, "Physiologic gastrectomy," British Journal of Surgery, vol. 33, article 146, 1945.

Fang S jiang, Daram SR, Wu R, Bhaijee F. Pathogenesis, diagnosis, and management of gastric ischemia. Clin Gastroenterol Hepatol. 2014;12(2):246-252.e1. doi:10.1016/j.cgh.2013.07.025.

Mechanick JI, Youdim A, Jones DB, Timothy Garvey W, Huriey DL, Molly McMahon M, et al. Clinical practice guidelines for the perioperative nutritional, metabolic, and nonsurgical support of the bariatric surgery patient—2013 update: cosponsored by American Association of Clinical Endocrinologists, the Obesity Society, and American Society or Metabolic & Bariatric Surgery. Surg Obes Relat Dis 2013;9: 159-91. https://doi.org/10.1016/j.soard.2012.12.010 [PMID:23537696].

Rubino F, Nathan DM, Eckel RH, Schauer PR, Alberti KGMM, Zimmet PZ, et al. Met-abolic surgery in the treatment algorithm for type 2 diabetes: a joint statement by international diabetes organizations. Surg Obes Relat Dis 2016;12:1144-62. https://doi.org/10.1016/j.soard.2016.05.018.

Koh CY, Inaba CS, Sujatha-Bhaskar S, Hohmann S, Ponce J, Nguyen NT. Laparoscopic adjustable gastric band explantation and implantation at academic centers. J Am Coll Surg 2017;225:532-7. https://doi.org/10.1016/j.amcollsurg.2017.06.015 [PMID:28754410].

Albaugh VL, Abumrad NN. Surgical treatment of obesity. F1000Res 2018;7. https://doi.org/10.12688/f1000research.13515.1 [PMID:29904577].

Peterli R, Wölnerhanssen BK, Peters T, Vetter D, Kröll D, Borbély Y, et al. Effect of laparoscopic sleeve gastrectomy vs laparoscopic Roux-en-Y gastric bypass on weight loss in patients with morbid obesity: the SM-BOSS randomized clinical trial. JAMA 2018;319:255-65. https://doi.org/10.1001/jama.2017.20897 [PMID:29340679].

Salminen P, Helmio M, Ovaska J, Juuti A, Leivonen M, Peromaa-Haavisto P, et al. Ef-fect of laparoscopic sleeve gastrectomy vs laparoscopic Roux-en-Y gastric bypass on weight loss at 5 years among patients with morbid obesity: the SLEEVEPASS randomized clinical trial. JAMA 2018;319:241-54. https://doi.org/10.1001/jama.2017.20313 [PMID:29340676].

Kehagias I, Karamanakos SN, Argentou M, Kalfarentzos F. Randomized clinical trial of laparoscopic Roux-en-Y gastric bypass versus laparoscopic sleeve gastrectomy for the management of patients with BMI b50 kg/m2. Obes Surg 2011;21:1650-6. https://doi.org/10.1007/s11695-011-0479-x [PMID:21818647].

Puzziferri N, Roshek TB, Mayo HG, Gallagher R, Belle SH, Livingston EH. Long-term follow-up after bariatric surgery a systematic review. JAMA 2014;312:934-42. https://doi.org/10.1001/jama.2014.10706 [PMID:25182102].

Courcoulas AP, Christian NJ, Belle SH, Berk PD, Flum DR, Garcia L, et al. Weight change and health outcomes at 3 years after bariatric surgery among individuals with severe obesity. JAMA 2013;310:2416-25. https://doi.org/10.1001/jama.2013.280928 [PMID:24189773].

Maciejewski ML, Arterburn DE, Van Scoyoc L, Smith VA, Yancy WS, Weidenbacher HJ, et al. Bariatric surgery and long-termdurability of weight loss. JAMA Surg 2016; 151:1046. https://doi.org/10.1001/jamasurg.2016.2317.

O'Brien PE, MacDonald L, AndersonM, Brennan L, BrownWA. Long-termoutcomes after bariatric surgery. Ann Surg 2013;257:87-94. https://doi.org/10.1097/sla. 0b013e31827b6c02.

Adams TD, Davidson LE, Litwin SE, Kim J, Kolotkin RL, Nanjee MN, et al. Weight and metabolic outcomes 12 years after gastric bypass. N Engl J Med 2017;377:1143-55. https://doi.org/10.1056/NEJMoa1700459 [PMID:28930514].

Wolnerhanssen B, Peterli R. State of the art: sleeve gastrectomy. Dig Surg 2014;31:40-7. https://doi.org/10.1159/000354320 [PMID:24819496].

Osland E, Yunus RM, Khan S, Memon B, Memon MA. Weight loss outcomes in lap-aroscopic vertical sleeve gastrectomy (LVSG) versus laparoscopic Roux-en-Y gas-tric bypass (LRYGB) procedures: a meta-analysis and systematic review of randomized controlled trials. Surg Laparosc Endosc Percutan Tech 2017;27:8-18. https://doi.org/10.1097/SLE.0000000000000374.

Vitiello A, Pilone V, Ferraro L, Forestieri P. Is the sleeve gastrectomy always a better procedure? Five-year results from a retrospective matched case-control study. Obes Surg 2018. https://doi.org/10.1007/s11695-018-3161-8 [PMID:29549660].

(56) References Cited

OTHER PUBLICATIONS

Risstad H, Søvik TT, Engström M, Aasheim ET, Fagerland MW, Olsén MF, et al. Five-year outcomes after aparoscopic gastric bypass and laparoscopic duode-nal switch in patients with body mass index of 50 to 60: a randomized clinical trial. JAMA Surg 2015;150:352-61. https://doi.org/10.1001/jamasurg.2014. 3579 [PMID:25650964].

Marceau P, Biron S, Marceau S, Mould F-S, Lebel S, Lescelleur O, et al. Long-term metabolic outcomes 5 to 20 years after biliopancreatic diversion. Obes Surg 2015;25:1584-93. https://doi.org/10.1007/s11695-015-1599-5.

Apovian CM, Shah SN, Wolfe BM, Ikramuddin S, Miller CJ, Tweden KS, et al. Two- year outcomes of vagal nerve blocking (vBloc) for the treatment of obesity in the ReCharge trial. Obes Surg 2017;27:169-76. https://doi.org/10.1007/s11695-016- 2325-7 [PMID:27506803].

Sarr MG, Billington CJ, Brancatisano R, Brancatisano A, Toouli J, Kow L, et al. The EMPOWER study: randomized, prospective, double-blind, multicenter trial of vagal blockade to induce weight loss in morbid obesity. Obes Surg 2012;22: 1771-82. https://doi.org/10.1007/s11695-012-0751-8 [PMID:22956251].

Committee CI. ASMBS policy statement on gastric plication. Surg Obes Relat Dis 2011;7:262. https://doi.org/10.1016/j.soard.2011.03. 004 [PMID:21621164].

Barrichello S, Minata MK, Garcia Ruiz de Gordejuela A, BernardoWM, de Souza TF, Galvão Neto M, et al. Laparoscopic greater curvature plication and laparoscopic sleeve gastrectomy treatments for obesity: systematic review and meta-analysis of short- and mid-term results. Obes Surg 2018. https://doi.org/10.1007/s11695- 018-3330-9.

Armijo PR, Pagkratis S, Boilesen E, Tanner T, Oleynikov D. Growth in robotic-assisted procedures is from conversion of laparoscopic procedures and not from open surgeons' conversion: a study of trends and costs. Surg Endosc 2018;32:2106-13. https://doi.org/10.1007/s00464-017-5908-z [PMID:29067582].

Magouliotis DE, Tasiopoulou VS, Sioka E, Zacharoulis D. Robotic versus laparoscopic sleeve gastrectomy for morbid obesity: a systematic review and meta-analysis. Obes Surg 2017;27:245-53. https://doi.org/10.1007/s11695-016-2444-1 [PMID:27815863].

Genco A, Ernesti I, Ienca R, Casella G, Mariani S, Francomano D, et al. Safety and efficacy of a new swallowable intragastric balloon not needing endoscopy: Early Italian experience. Gastrointest Endosc 2017;85:1-5. doi: 10.1007/s11695-017-2877-1.

Imaz I, Martinez-Cervell C, Garcia-Alvarez EE, Sendra-Gutiérrez JM, Gonzalez-Enriquez J. Safety and effectiveness of the intragastric balloon for obesity. A meta-analysis. Obes Surg 2008;18(7):841-6.

Abd Ellatif ME, Alfalah H, Asker WA, El Nakeeb AE, Magdy A, Thabet W, et al. Place of upper endoscopy before and after bariatric surgery: A multicenter experience with 3219 patients. World J Gastrointest Endosc 2016;8:409-17. doi: 10.4253/wjge. v8.i10.409.

Marinos G, Eliades C, Raman Muthusamy V, Greenway F. Weight loss and improved quality of life with a nonsurgical endoscopic treatment for obesity: Clinical results from a 3- and 6-month study. Surg Obes Relat Dis 2014;10:929-34. doi: 10.1016/j.soard.2014.03. 005.

Sullivan S, Stein R, Jonnalagadda S, Mullady D, Edmundowicz S. Aspiration therapy leads to weight loss in obese subjects: a pilot study. Gastroenterology 2013;145(6):1245.

Thompson CC, Dayyeh BKA, Kushner R, et al. 381 the AspireAssist is an effective tool in the treatment of class II and class III obesity: results of a one-year clinical trial. Gastroenterology 2016;150(4 Suppl. 1):S86.

Courcoulas A, Abu Dayyeh BK, Eaton L, et al. Intragastric balloon as an adjunct to lifestyle intervention: a randomized controlled trial. Int J Obes (2005) 2017;41(3):427-33.

Ponce J, Woodman G, Swain J, et al. The REDUCE pivotal trial: a prospective, randomized controlled pivotal trial of a dual intragastric balloon for the treatment of obesity. Surg Obes Relat Dis 2015;11(4):874-81.

Thompson CC, Chand B, Chen YK, et al. Endoscopic suturing for transoral outlet reduction increases weight loss after Roux-en-Y gastric bypass surgery. Gastroenterology 2013;145(1):129-37.e123.

Jirapinyo P, Thompson CC. Endoscopic bariatric and metabolic therapies: surgical analogues and mechanisms of action. Clin Gastroenterol Hepatol 2017;15: 619-30. https://doi.org/10.1016/j.cgh.2016.10.021 [PMID:27989851].

Stenberg E, Szabo E, Agren G, Näslund E, Boman L, Bylund A, et al. Early complica-tions after laparoscopic gastric bypass surgery: results from the Scandinavian Obe-sity Surgery Registry. Ann Surg 2014;260:1040-7. https://doi.org/10.1097/SLA. 0000000000000431 [PMID:24374541].

Mizadeh RF, Li S, Inaba C, Penalosa P, Hinojosa MW, Smith BR, et al. Risk factors for gastrointestinal leak after bariatric surgery: MBASQIP analysis. J AmColl Surg 2018; 227:135-41.

Haskins IN, Ju T, Whitlock AE, Rivas L, Amdur RL, Lin PP, et al. Older age confers a higher risk of30-day morbidity and mortality following laparoscopic bariatric sur-gery: an analysis of the metabolic and bariatric surgery quality improvement pro-gram. Obes Surg 2018. https://doi.org/10.1007/s11695-018-3233-9 [PMID:29663253].

Mala T, Høgestøl I. Abdominal pain after Roux-En-Y gastric bypass for morbid obesity. Scand J Surg 2018. https://doi.org/10.1177/1457496918772360 [1457496918772360; PMID:29739280].

Coblijn UK, Goucham AB, Lagarde SM, Kuiken SD, van Wagensveld BA. Development of ulcer disease after Roux-en-Y gastric bypass, incidence, risk factors, and patient presentation: a systematic review. Obes Surg 2014;24:299-309. https://doi.org/10.1007/s11695-013-1118-5 [PMID:24234733].

Coblijn UK, Lagarde SM, de Castro SM, Kuiken SD, van Wagensveld BA. Symptomatic marginal ulcer disease after Roux-en-Y gastric bypass: incidence, risk factors and management. Obes Surg 2015;25:805-11. https://doi.org/10.1007/s11695- 014-1482-9 [PMID:25381115].

Geubbels N, Lijftogt N, Fiocco M, van Leersum NJ, Wouters MW, de Brauw LM. Meta-analysis of internal herniation after gastric bypass surgery. Br J Surg 2015; 102:451-60. https://doi.org/10.1002/bjs.9738 [PMID:25708572].

Greenstein AJ, O'Rourke RW. Abdominal pain after gastric bypass: suspects and solutions. Am J Surg 2011;201:819-27. https://doi.org/10.1016/j.amjsurg.2010.05. 007 [PMID:21333269].

Bal BS, Finelli FC, Shope TR, Koch TR. Nutritional deficiencies after bariatric sur-gery. Nat Rev Endocrinol 2012;8:544-56. https://doi.org/10.1038/nrendo. 2012.48.

Weng TC, Chang CH, Dong YH, Chang YC, Chuang LM. Anaemia and related nutrient deficiencies after Roux-en-Y gastric bypass surgery: a systematic review and meta-analysis. BMJ Open 2015;5:e006964. https://doi.org/10.1136/omjopen-2014- 006964 [PMID:26185175].

Maghrabi AH, Wolski K, Abood B, Licata A, Pothier C, Bhatt DL, et al. Two-year out- comes on bone density and fracture incidence in patients with T2DM randomized to bariatric surgery versus intensive medical therapy. Obesity (Silver Spring) 2015; 23:2344-8. https://doi.org/10.1002/oby.21150 [PMID:26193177].

Rodriguez-Carmona Y, López-Alavez FJ, Gonzalez-Garay AG, Solis-Galicia C, Meléndez G, Serralde-Zíñiga AE. Bone mineral density after bariatric surgery. A systematic review. Int J Surg 2014;12:976-82. https://doi.org/10.1016Zj.jsu.2014. 08.002 [PMID:25110331].

Chakhtoura MT, Nakhoul NN, Shawwa K, Mantzoros C, El Hajj Fuleihan GA. Hypovitaminosis D in bariatric surgery: a systematic review of observational studies. Metabolism 2016;65:574-85. https://doi.org/10.1016/j.metabol.2015.12.004.

Zhang Q, Chen Y, Li J, Chen D, Cheng Z, Xu S, et al. A meta-analysis of the effects of bariatric surgery on fracture risk. Obes Rev 2018;19:728-36. https://doi.org/10. 1111/obr.12665.

Emous M, Wolffenbuttel BHR, van Dijk G, Totté E, van Beek AP. Long-term self-reported symptom prevalence of early and late dumping in a patient population after sleeve gastrectomy, primary, and revisional gastric bypass surgery. Surg Obes Relat Dis 2018. https://doi.org/10.1016/j.soard.2018.04.011 [PMID:29858129].

Nielsen JB, Pedersen AM, Gribsholt SB, Svensson E, Richelsen B. Prevalence, sever-ity, and predictors of symptoms of dumping and

(56) References Cited

OTHER PUBLICATIONS hypoglycemia after Roux-en-Y gastric bypass. Surg Obes Relat Dis 2016;12:1562-8. https://doi.org/10.1016/j.soard.2016.04.017.

Berger ER, Clements RH, Morton JM, Huffman KM, Wolfe BM, Nguyen NT, et al. The impact of different surgical techniques on outcomes in laparo-scopic sleeve gastrectomies: the first report from the metabolic and bariatric surgery accreditation and quality improvement program (MBSAQIP). Ann Surg 2016;264:464-73. https://doi.org/10.1097/SLA.0000000000001851 [PMID:27433904].

Dhar VK, Hanseman DJ, Watkins BM, Paquette IM, Shah SA, Thompson JR. What mat-ters after sleeve gastrectomy: patient characteristics or surgical technique. Surgery 2018;163:571-7. https://doi.org/10.1016/j.surg.2017.09.052 [PMID:29398036].

Ibrahim AM, Thumma JR, Dimick JB. Reoperation and Medicare expenditures after laparoscopic gastric band surgery. JAMA Surg 2017;152:835-42 https://doi.org/10. 1001/jamasurg.2017.1093 [PMID:28514487].

Nguyen NT, Kim E, Vu S, Phelan M. Ten-year outcomes ofa prospective random-ized trial of laparoscopic gastric bypass versus laparoscopic gastric banding. Ann Surg 2018;268:106-13. https://doi.org/10.1097/SLA.0000000000002348 [PMID:28692476].

Arterburn D, Powers JD, Toh S, Polsky S, Butler MG, Portz JD, et al. Comparative ef-fectiveness of laparoscopic adjustable gastric banding vs laparoscopic gastric by-pass. JAMA Surg 2014;149:1279-87. https://doi.org/10.1001/jamasurg.2014.1674[PMID:25353723].

Sharples AJ, Charalampakis V, Daskalakis M, Tahrani AA, Singhal R. Systematic re-view and meta-analysis of outcomes after revisional bariatric surgery following a failed adjustable gastric band. Obes Surg 2017;27:2522-36. https://doi.org/10.1007/s11695-017-2677-7 [PMID:28477245].

Committee Cl. ASMBS policy statement on gastric plication. Surg Obes Relat Dis 2011;7:262. https://doi.org/10.1016/j.soard.2011.03.004 [PMID:21621164].

Stefanidis D, Bailey SB, Kuwada T, Simms C, Gersin K. Robotic gastric bypass may lead to fewer complications compared with laparoscopy. Surg Endosc 2018;32: 610-6. https://doi.org/10.1007/s00464-017-5710-y [PMID:28726145].

Betzel B, Drenth JPH, Siersema PD. Adverse events of the duodenal-jejunal bypass liner a systematic review. Obes Surg 2018. https://doi.org/10.1007/s11695-018- 3441-3 [PMID:30121857].

Tate CM, Geliebter A. Intragastric balloon treatment for obesity: FDA safety up-dates. Adv Ther 2018;35:1-4. https://doi.org/10.1007/s12325-017-0647-z [PMID:29285708].

Kumbhar V, Oberbach A, Nimgaonkar A. Primary endoscopic therapies for obesity and metabolic diseases. Curr Opin Gastroenterol 2015; 31(5):351-8.

ASGE Bariatric Endoscopy Task Force and ASGE Technology Committee, Abu Dayyeh BK, Kumar N, et al. ASGE Bariatric Endoscopy Task Force systematic review and meta-analysis assessing the ASGE PIVI thresholds for adopting endoscopic bariatric therapies. Gastrointest Endosc 2015;82(3):425-3800000.

Acosta A, Streett S, Kroh MD, et al. White paper Aga: POWER—practice guide on obesity and weight management, education, and resources. Clin Gastroenterol Hepatol 2017;15(5):631. 304415744.

Kumar N, Thompson CC. Transoral outlet reduction for weight regain after gastric bypass: long-term follow-up. Gastrointest Endosc 2016;83(4):776-9.

Pajot G, Calderon G, Acosta A. Endoscopic treatments for obesity. Curr Treat Options Gastroenterol 2017;15:660-75. doi: 10.1007/s11938-017-0158-7.

Weiner JP, Goodwin SM, Chang HY, Bolen SD, Richards TM, Johns RA, et al. Impact otbariatric surgery on health care costs ofobese persons: a 6-year follow-up ofsur-gical and comparison cohorts using health plan data. JAMA Surg 2013;148:555-62. https://doi.org/10.1001/jamasurg.2013.1504 [PMID:23426865].

Alsumali A, Eguale T, Bairdain S, Samnaliev M. Cost-effectiveness analysis of bariat-ric surgery for morbid obesity. Obes Surg 2018. https://doi.org/10.1007/s11695- 017-3100-0 [PMID:29335933].

KimDD, Arterbum DE, Sullivan SD, Basu A. Economic value ofgreater access to bar- iatric procedures for patients with severe obesity and diabetes. Med Care 2018;56: 583-8. https://doi.org/10.1097/mlr.0000000000000924.

Hennings DL, Baimas-George M, Al-Quarayshi Z, Moore R, Kandil E, DuCoin CG. The inequity of bariatric surgery publicly insured patients undergo lower rates of bar-iatric surgery with worse out-comes. Obes Surg 2018;28:44-51. https://doi.org/10. 1007/s11695-017-2784-5.

Funk LM, Jolies SA, Greenberg CC, Schwarze ML, Safdar N, McVay MA, et al. Primary care physician decision making regard-ing severe obesity treatment and bariatric surgery: a qualitative study. Surg Obes Relat Dis 2016;12:893-901. https://doi. org/10.1016/j.soard.2015.11.028 [PMID:26948943].

Funk LM, Jolies S, Fischer LE, Voils CL Patient and referring practitioner characteristics associated with the likelihood of under-going bariatric surgery. JAMA Surg 2015;150:999. https://doi.org/10.1001/jamasurg.2015.1250.

Simon R, Lahiri SW. Provider practice habits and barriers to care in obesity management in a large multicenter health system. Endocr Pract 2018;24:321-8. https:// doi.org/10.4158/EP-2017-0221.

Choi HS, Chun HJ. Recent trends in endoscopic bariatric therapies. Clin Endosc 2017;50:11-16].

Dargent J. Novel endoscopic management of obesity. Clin Endosc. 2016;49(1):30-36. doi:10.5946/ce.2016.49.1.30.

American Society for Metabolic and Bariatric Surgery Position State-ment on emerging endosurgical interventions for treatment of obesity. Surg Obes Relat Dis 2009;5:297-298].

\* cited by examiner

LOW RISK, REVERSIBLE, WEIGHT LOSS PROCEDURE

BACKGROUND OF THE INVENTION

Field of the Invention

The present disclosure relates generally to a medical procedure to reduce stomach volume. More particularly the present disclosure relates to an endoscopic and minimally invasive method of reducing stomach volume.

Description of Related Art

Obesity is a major health issue throughout much of the world, especially in the United States. In 2015, it was estimated that 107.7 million children and 603.7 million adults were obese worldwide. Over one third of American adults are obese, and obesity rates continue to increase.

While dieting, exercising, and medicinal solutions exist, weight loss surgery (WLS) is the most effective intervention to reduce body weight and obesity-associated diseases among obese patients and has become a widely accepted approach to treating these disorders. However, there are many shortcomings of the existing weight loss surgery procedures. Many involve accessing the stomach surgically, which has numerous related dangers. Also, many procedures cut and/or suture the stomach. This causes trauma to the stomach tissue as well as the related risks of anesthetics, as well as infection, and the like which result from any cutting or puncturing of bodily tissue. Further, many of these methods are complex, invasive, and require substantial recovery time and dietary shifts to allow the body to heal and to allow the stomach to resume normal operation. All of these factors lead to weight loss surgery and the existing procedures being expensive and risky.

SUMMARY OF THE INVENTION

The subject matter of this application may involve, in some cases, interrelated products, alternative solutions to a particular problem, and/or a plurality of different uses of a single system or article.

In one aspect, a method of reducing stomach volume is provided. The method involves gathering a quantity of stomach tissue of a stomach of a patient, and securing the gathered quantity of stomach tissue in the gathered position so as to reduce a volume of the stomach of the patient.

In another aspect, an endoscopic method of reducing stomach volume is provided. The method involves inserting an endoscope comprising at least one tool into a stomach of a patient. The endoscope and tool are used for gathering a quantity of stomach tissue of the stomach of the patient, and for securing the gathered quantity of stomach tissue in the gathered position so as to reduce the effective volume of the stomach of the patient.

DETAILED DESCRIPTION

Figure 1:
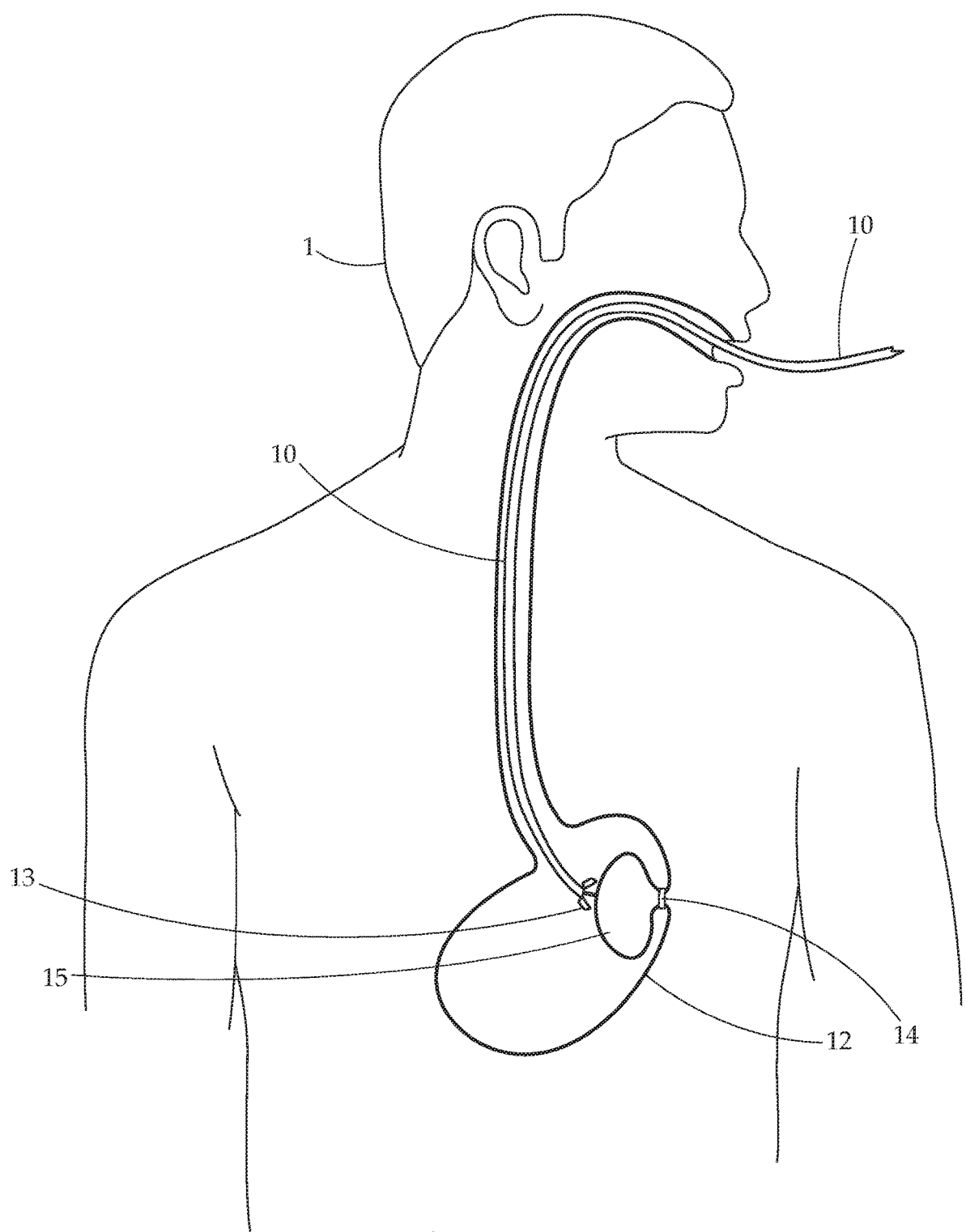
FIG. 1 provides an endoscopic embodiment of the performance of the procedure is shown.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

The present invention solves many problems of the prior art. The present disclosure relates to a new medical weight loss procedure which reduces stomach volume by gathering a portion of the stomach tissue together and holding it in place. This draws the remainder of the stomach closer together, reducing the effective stomach volume. The procedure may be done endoscopically in certain embodiments, greatly minimizing its invasiveness and greatly increasing the speed of the procedure and recovery. The stomach and other gastrointestinal organs, in most embodiments, remain fully intact, which can allow the procedure to be reversed easily. This procedure also allows the body to be able to process food as before the procedure, with no nutrient deficiencies as is experienced in many other procedures. In many cases, the procedure disclosed herein can be used for patients with conditions that may not make them eligible for other treatment methods, such as children and slightly overweight individuals. Further still, typically there will be limited post-procedure restrictions, such as type of food or food quantity limits as is the case with other prior art methods. Prior art procedures often require a liquid only diet, proceeding to soft food and then finally regular food which adds recovery challenges.

Generally, the method of this disclosure involves the gathering of a portion of stomach tissue and then securing it in place so as to decrease the overall effective volume of the stomach. Care may be taken to secure the stomach tissue together gently, so as not to damage the tissue or excessively cut off blood flow. In so doing, the feeling of satiety is achieved with a much smaller amount of food, without restriction on type or quality of food. For example, the stomach tissue may be gathered into a ball or other shape, and then held in place by a wrap, band, tie, ring, band, covering, net, balloon, and the like. By gathering up the stomach tissue and holding it in place, the effective stomach volume is reduced in a way which avoids the cutting or external access limitations of the prior art procedures.

The gathering discussed herein refers to the bringing together of stomach tissue. This may be done in any number of ways, and the gathering is used generally to discuss a way to reduce the effective stomach volume by adjusting the shape of the stomach from its natural shape to reduce volume. As discussed below, the gathering may be in the form of bringing the stomach tissue into a ball, drawing it inwards, folding it, wrapping it, and so on. Non-limiting examples of the gathering are also shown in the figures, as discussed in detail below.

In a particular embodiment, the procedure of reducing the effective stomach volume will be performed endoscopically using an endoscope. For example, an endoscope with appropriate tools may be inserted through the patient's esophagus (via either the mouth or the nose) and into the stomach. The endoscope will be guided to a predetermined area of the stomach, and tools of the endoscope will be used to gather a predetermined amount of the stomach tissue together, for example into a ball or similar shape, and then to wrap a tie or similar retainer structure around the gathered tissue to hold it in place. The endoscope may use any type of tool or tools to achieve the stomach tissue gathering. For example, a suction tool may be used to draw the stomach tissue in, and then a pincer or other manipulating tool may be used to apply the tie to hold the tissue together. In another embodiment a grasping or pincer tool may be used to grab a portion or portions of the stomach tissue, and draw it inward, and then another pincer or other manipulating tool may be used to apply the tie to hold the tissue together. In some embodiments, the stomach tissue may be gathered and held in place at more than one location, depending on desired results, patient needs, and stomach configuration. For convenience, this gathered and held stomach tissue will be referred to as a "ball" though of course it need not be in that shape. This procedure may be carried out by a person operating the endoscope (or other device used to carry out the procedure), or may be performed by a computerized robotics machine.

The amount of stomach tissue gathered, and thus the amount of effective stomach volume reduced, will vary from patient to patient. The amount will depend on the existing size of the stomach and the anticipated and/or desired weight loss rate.

In many instances, the stomach ball may be untied or otherwise released allowing the procedure to be reversed. The stomach will then revert to close to its previous size and shape. Further, in other embodiments, the stomach ball may be cut and stitched to completely remove the stomach tissue after it is gathered. In a further particular embodiment, the endoscope may hold the removed stomach tissue and bring it out of the body when the endoscope is removed. However, this cutting is not performed in most embodiments so as to allow for a safer, quicker, less invasive, reversible procedure with a quicker recovery time compared to the prior art methods which involve cutting large sections of the stomach tissue.

In certain embodiments, the stomach tissue ball may be secured by a band which may wrap around part of the gathered stomach tissue to hold it in place. In one embodiment, the band may be able to be tightened and/or loosened remotely. For example, a small motor engaged with the band may allow for the tightening or loosening. A signal receiver or transceiver may be in communication with the motor and capable of activating the motor upon receipt of a signal. This arrangement allows for adjustment of the band remotely from outside of the body.

In various embodiments, this band (or whatever other structure is used to hold the tissue together, examples of which are provided above) may comprise a marker to allow it to be identified from outside the body. For example, the marker may be identifiable by radiation, through ultrasound or x-ray, magnetically, as an RFID chip, and the like. For example, the marker may be selected of a material which is opaque when viewed on an X-ray or ultrasound.

While the present procedure has been discussed largely in terms of an endoscopic procedure, it should be understood that this is not necessarily required. Indeed, the disclosure relates to any procedure which can reduce effective stomach volume by gathering together stomach tissue and holding it in place, endoscopically or otherwise.

Turning now to FIG. 1, an endoscopic embodiment of the performance of the procedure is shown. In this view, the patient 1 has the endoscope 10 passing through the mouth and esophagus and into the stomach 12. The endoscope tool 13 has gathered stomach tissue from an interior of the stomach and formed it into a ball type shape 15. A band 14 is wrapped around the stomach tissue to hold the gathered tissue in place, thereby securing the stomach in a reduced-volume position compared to its original volume without the gathered stomach tissue 15. As shown in this figure, the procedure is performed on the greater curvature of the stomach in this embodiment, though any area of the stomach may be used.

Figure 2:
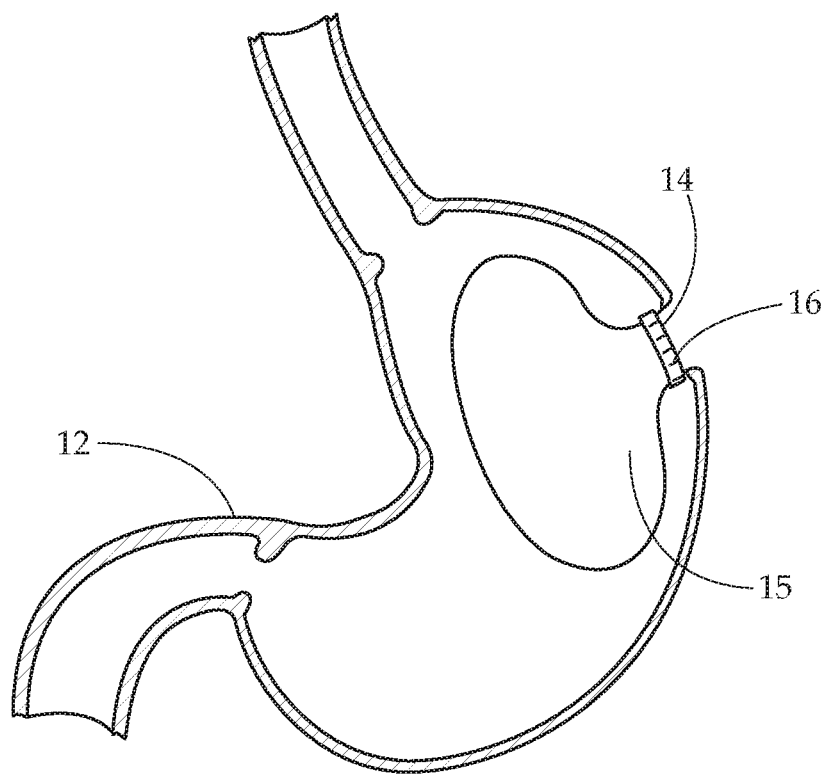
FIG. 2 provides a detail view of an embodiment of the gathered stomach tissue.

FIG. 2 provides a detail view of an embodiment of the gathered stomach tissue ball. In this view, the stomach tissue is gathered and formed into a ball 15. A band 14 separates the gathered ball 15 from the remainder of the stomach 12. This band 14 comprises a marker 16, which may be any marker which allows identification of the location of the band 14.

Figure 3:
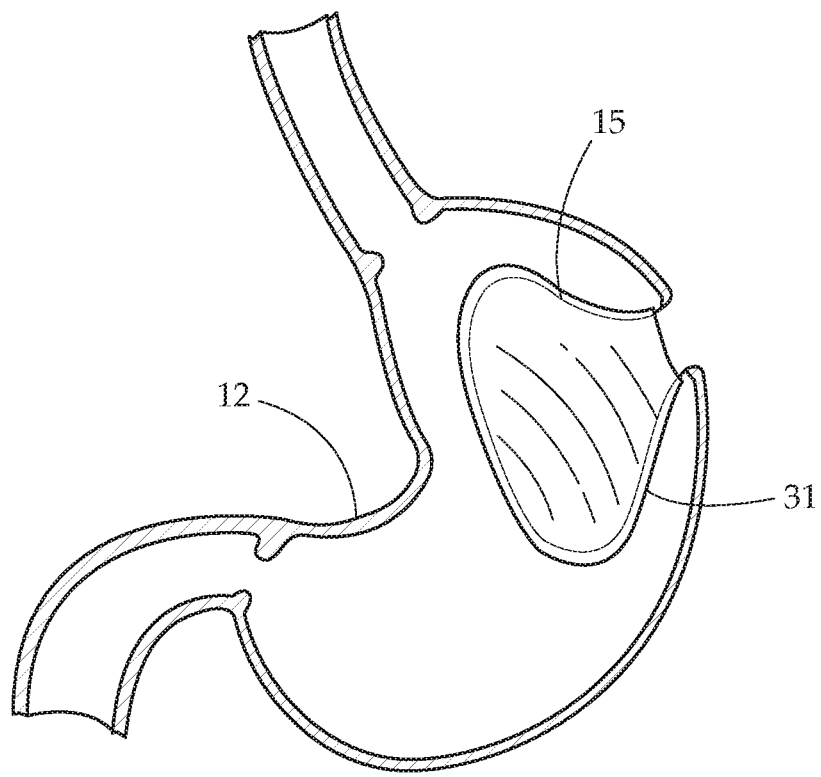
FIG. 3 provides a detail view of an embodiment of the gathered stomach tissue FIG. 4 provides a view of an embodiment of the procedure using a suction endoscope tool.

FIG. 3 provides a detail view of an embodiment of the gathered stomach tissue "ball." In this view, a net or mesh wrap 31 surrounds the gathered stomach tissue ball 15, holding it together and in place. Of course, the wrap 13 may be made of any material, permeable or not, without straying from the scope of this invention.

Figure 4:
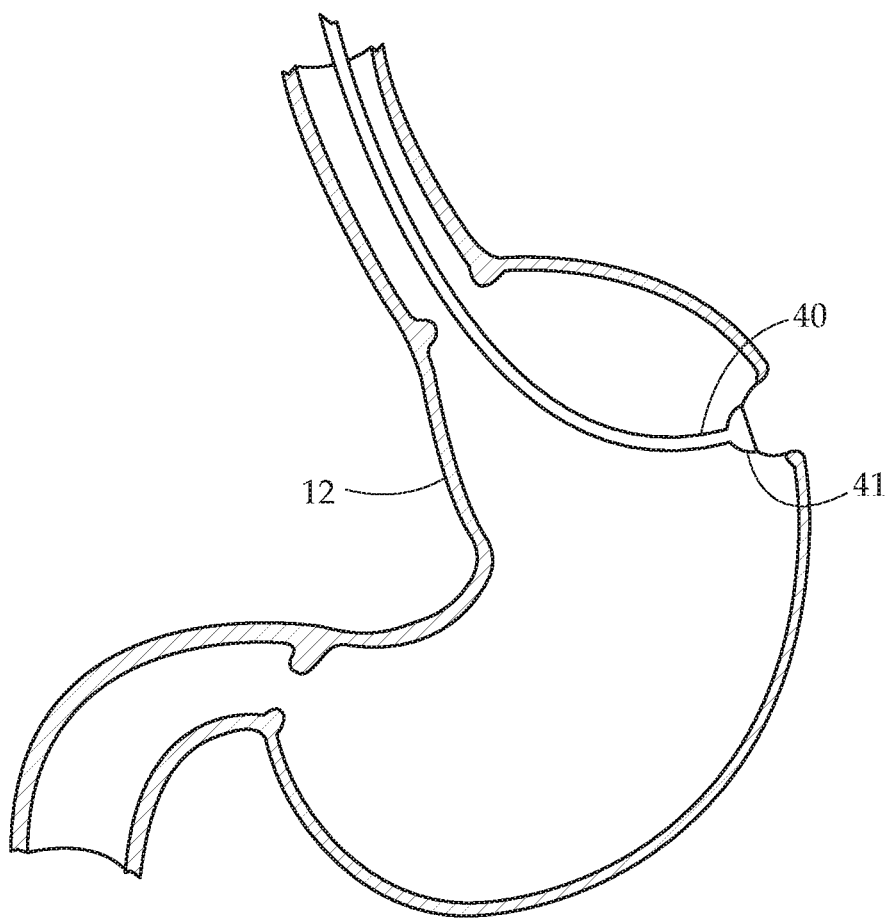

FIG. 4 provides a view of an embodiment of the procedure using a suction endoscope tool. In this embodiment, an area of the stomach 12 is contacted by a suction cup 41. A low pressure is drawn through tube 40, causing the stomach tissue to be drawn into, and held by, the cup 41. From there, the cup 41 may be drawn away from the rest of the stomach 12, gathering the stomach tissue. This gathered tissue may then be secured together (not shown) so as to reduce the effective volume of the stomach 12.

Figure 5:
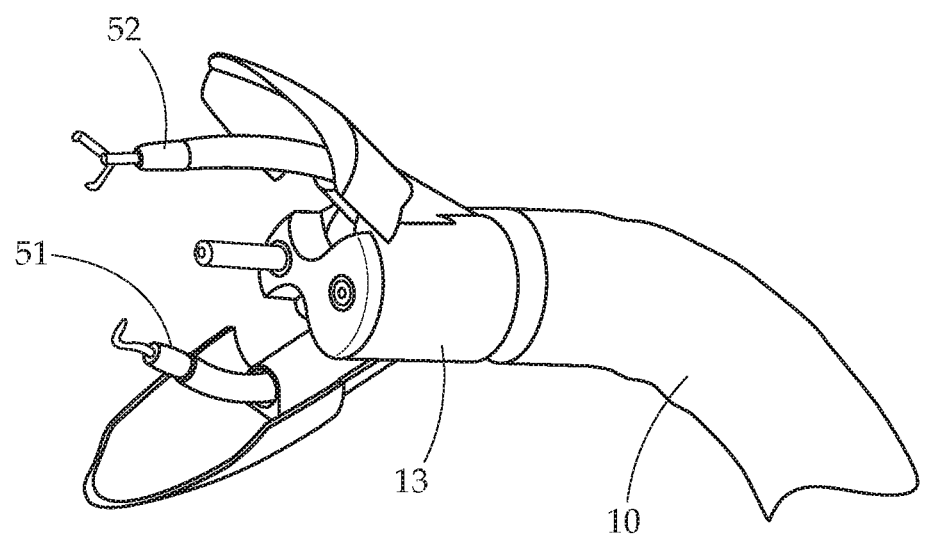
FIG. 5 provides a view of an embodiment of an endoscope and endoscopic tools.
Figure 6:
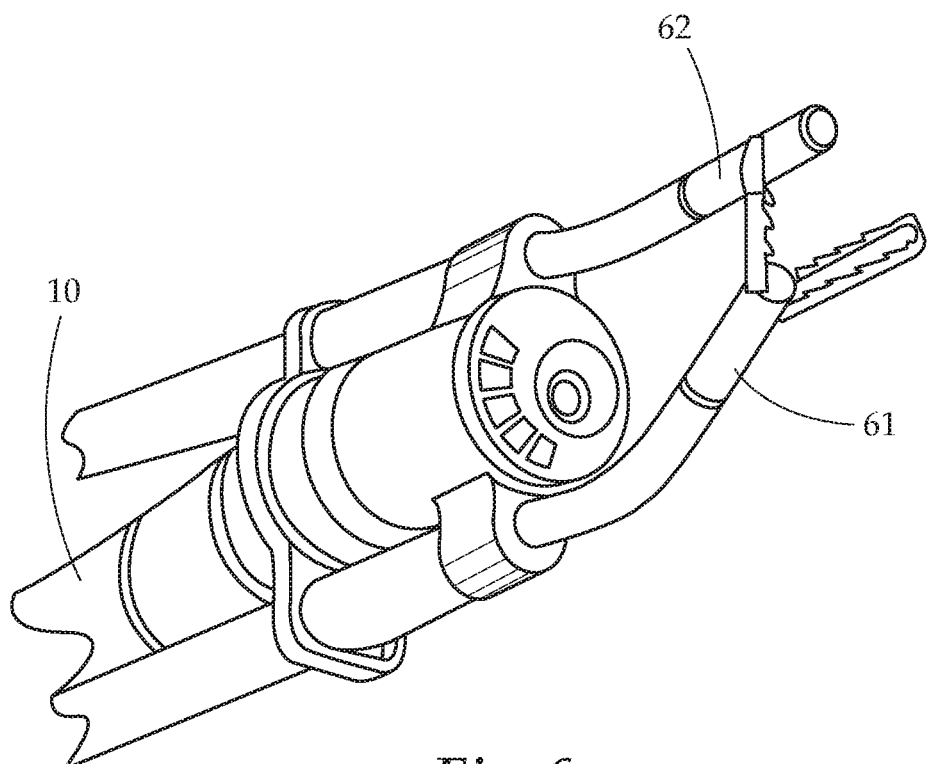
FIG. 6 provides a view of an embodiment of an endoscope and endoscopic tools.

FIGS. 5 and 6 provide exemplary embodiments of tools of endoscopes which may be used to perform the procedure of the subject disclosure. FIG. 5 provides an embodiment of the endoscope 10 having tools 52 and 51. These tools 52, 51 are movable and operable by the endoscope operator. Tool 52 is a pincer which can hold a portion of stomach tissue and draw it to a gathered position, in some cases with the aid of tool 51 which is a hook. Once gathered, these tools may then be used to secure the tissue in place, using any one or more of the various structures disclosed above, or any other method or structure to secure the tissue together and in place. FIG. 6 provides an embodiment of the endoscope 10 having tools 62 and 61. Tool 61 is a pincer, while tool 62 is movable as a finger to push, hold, and guide as needed. The tools, alone or in combination can be used to gather a portion of stomach tissue together. In some cases, an endoscope having three tools is used, with two tools holding the stomach tissue, and a third applying the band (or other structure) to secure the gathered stomach tissue. The endoscope 10 tools 61, 62 may then be used to secure the gathered tissue in place using any of the structures disclosed above, or any other method or structure.

In one embodiment of the securing of the stomach tissue using an endoscope and tool(s), a pincer tool may hold open a ring or band and pass it over the gathered tissue, the ring or band may then be tightened, tied, or otherwise tightened to secure the stomach tissue in place. If the ring is elastic, it may be stretched wide and then allowed to relax to a tightened position to secure the stomach tissue in place. A similar operation may be performed with two finger type endoscope tools to hold opposite sides of the ring/band etc. In another embodiment, two pincer tools may be used to hold opposite ends of a tie, each tool can bring the opposite sides together over the gathered tissue and connect them, holding the tissue in the gathered position.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth. Moreover, while certain aspects of the invention are disclosed with certain embodiments, it is to be understood that these different aspects of the embodiments may be combined and interchanged with other embodiments. Indeed by this written disclosure, any element, step, or other aspect of one disclosed embodiment may be equally applied to any other embodiment without straying from the scope of this invention.

What is claimed is:

1. A method of reducing stomach volume comprising the steps of:
   gathering together, from an inside of the stomach, a quantity of stomach tissue of a stomach of a patient wherein the stomach tissue is gathered into a ball shape; and
   securing, on the inside of the stomach, the gathered quantity of stomach tissue in a gathered position so as to reduce a volume of the stomach of the patient;
   wherein the step of securing the stomach tissue in the gathered position allows blood flow to the gathered quantity of stomach tissue and the method of reducing the stomach volume keeps the stomach fully intact,
   the gathering step and securing step are performed without a cutting of any tissue of the patient;
   wherein the gathering step and securing step are done endoscopically using an endoscope, the endoscope comprising two separately operable tools, the first of the two separately operable tools being a pincer tool.

2. The method of reducing stomach volume of claim 1 wherein the securing step is performed by tying a tie about a part of the gathered stomach tissue.

3. The method of reducing stomach volume of claim 1 wherein the securing step is performed by covering the gathered stomach tissue.

4. The method of reducing stomach volume of claim 1 wherein the securing step is performed by wrapping a band about a part of the gathered stomach tissue.

5. The method of reducing stomach volume of claim 4 wherein the band further comprises a marker.

6. The method of reducing stomach volume of claim 1 wherein the second of the two separately operable tools is a second pincer tool.

7. The method of reducing stomach volume of claim 6 wherein the securing step comprises the first pincer tool holding a first side of a ring or band, and the second pincer tool holding a second side of the ring or band, each tool bringing the opposite sides together over the gathered tissue and connecting the two sides of the ring or band, thereby holding the tissue in the gathered position.

8. The method of reducing stomach volume of claim 1 wherein the second of the two separately operable tools is a hook.

9. The method of reducing stomach volume of claim 1 wherein the second of the two separately operable tools is a vacuum tool.

10. The method of reducing stomach volume of claim 1 wherein the endoscope further comprises a third separately operable tool.

11. The method of reducing stomach volume of claim 1 wherein the pincer tool holds open a ring or band, and wherein the securing step comprises passing the ring or band over the gathered tissue.

12. A method of reducing stomach volume comprising the steps of:
   inserting an endoscope comprising a tool into a stomach of a patient;
   gathering together a quantity of stomach tissue of the stomach of the patient from an inside of the stomach; and
   securing the gathered quantity of stomach tissue in a gathered position on the inside of the stomach in a ball or egg shape, so as to reduce a volume of the stomach of the patient, wherein the step of securing the stomach tissue in the gathered position allows blood flow to the gathered quantity of stomach tissue and the method of reducing the stomach volume keeps the stomach fully intact;
   the gathering step and securing step are performed without a cutting of any tissue of the patient.

13. The method of reducing stomach volume of claim 12 wherein the securing step is performed by attaching one of a band, a tie, a ring, an adjustable band, a net, and a balloon about a portion of the gathered stomach tissue.

14. The method of reducing stomach volume of claim 12 wherein the securing step is performed by wrapping a band about a base of the gathered stomach tissue ball or egg shape.

15. The method of reducing stomach volume of claim 14 wherein the band further comprises a marker.

16. The method of reducing stomach volume of claim 12 wherein the tool is a suction cup tool, and wherein the gathering step comprises applying suction to an area of the stomach tissue using the suction cup tool.

17. The method of reducing stomach volume of claim 12 wherein the tool is a pincer, and wherein the gathering step comprises grasping a part of the stomach tissue using the pincer tool and drawing the stomach tissue towards a center of the stomach.

18. The method of reducing stomach volume of claim 12 wherein the securing step comprises applying one of a net, a mesh wrap, or a balloon surrounding the gathered stomach tissue ball or egg shape.

19. The method of reducing stomach volume of claim 12 further comprising the steps of:
   gathering together a second quantity of stomach tissue of the stomach of the patient; and
   securing the gathered second quantity of stomach tissue in a second gathered position so as to further reduce the volume of the stomach of the patient.

* * * * *